United States Patent
Su et al.

(10) Patent No.: US 9,655,517 B2
(45) Date of Patent: May 23, 2017

(54) PORTABLE EYE IMAGING APPARATUS

(71) Applicant: Visunex Medical Systems Co. Ltd., Grand Cayman (KY)

(72) Inventors: Wei Su, Sunnyvale, CA (US); Li Xu, San Ramon, CA (US)

(73) Assignee: Visunex Medical Systems Co. Ltd., Grand Cayman (KY)

( * ) Notice: Subject to any disclaimer, the term of this patent is extended or adjusted under 35 U.S.C. 154(b) by 0 days.

(21) Appl. No.: 13/757,798

(22) Filed: Feb. 3, 2013

(65) Prior Publication Data

US 2014/0085603 A1    Mar. 27, 2014

Related U.S. Application Data

(60) Provisional application No. 61/593,865, filed on Feb. 2, 2012.

(51) Int. Cl.
| | |
|---|---|
| *A61B 3/10* | (2006.01) |
| *A61B 3/117* | (2006.01) |
| *A61B 3/12* | (2006.01) |
| *A61B 3/14* | (2006.01) |
| *A61B 3/00* | (2006.01) |

(52) U.S. Cl.
CPC ............ *A61B 3/145* (2013.01); *A61B 3/0016* (2013.01); *A61B 3/0041* (2013.01); *A61B 3/12* (2013.01); *A61B 3/0008* (2013.01); *A61B 3/1173* (2013.01); *A61B 3/1176* (2013.01); *A61B 3/1208* (2013.01)

(58) Field of Classification Search
CPC ......... A61B 3/0008; A61B 3/10; A61B 3/117; A61B 3/12; A61B 3/1208; A61B 3/125; A61B 3/132; A61B 3/0016; A61B 3/0041; A61B 3/1173; A61B 3/1176; A61B 3/145

USPC ......................... 351/206–210, 219, 221, 245
See application file for complete search history.

(56) References Cited

U.S. PATENT DOCUMENTS

| | | | |
|---|---|---|---|
| 3,301,627 A | 1/1967 | Kimura | |
| 3,373,864 A | 3/1968 | Barton et al. | |
| 3,944,341 A | 3/1976 | Pomerantzeff | |
| 4,023,189 A | 5/1977 | Govignon | |
| 4,026,638 A | 5/1977 | Govignon | |
| 4,461,551 A * | 7/1984 | Blaha ..................... | A61B 3/132 351/214 |

(Continued)

FOREIGN PATENT DOCUMENTS

| | | |
|---|---|---|
| CN | 1170343 A | 1/1998 |
| CN | 101953675 A | 1/2011 |

(Continued)

OTHER PUBLICATIONS

Cho, N.H. et al. "Development of Real-Time Dual-Display Handheld and Bench-Top Hybrid-Mode SD-OCTs." Sensors 14 (2014): 2171-181.*

(Continued)

*Primary Examiner* — Thomas K Pham
*Assistant Examiner* — Nicholas R Pasko
(74) *Attorney, Agent, or Firm* — Shay Glenn LLP

(57) ABSTRACT

A portable digital imaging device, which utilizes the advanced features of wireless data transmission and high computing power of mobile computing devices in junction with the use miniature cameras and solid state lighting technology, is proposed as the next generation of medical imaging devices, in particular in ophthalmic imaging applications.

6 Claims, 7 Drawing Sheets

(56) References Cited

U.S. PATENT DOCUMENTS

| | | | |
|---|---|---|---|
| 5,036,446 A | 7/1991 | Quintanilla et al. | |
| 5,046,608 A | 9/1991 | Laipply | |
| 5,156,456 A | 10/1992 | Hoftman et al. | |
| 5,309,186 A * | 5/1994 | Mizuno | A61B 3/145 351/206 |
| 5,343,861 A | 9/1994 | Herman | |
| 5,455,644 A | 10/1995 | Yazawa et al. | |
| 5,506,634 A | 4/1996 | Wei et al. | |
| 5,537,127 A | 7/1996 | Jingu | |
| 5,537,162 A | 7/1996 | Hellmuth et al. | |
| 5,543,865 A | 8/1996 | Nanjo | |
| 5,608,472 A | 3/1997 | Szirth et al. | |
| 5,745,212 A | 4/1998 | Volk | |
| 5,751,396 A * | 5/1998 | Masuda | A61B 3/145 351/208 |
| 5,822,036 A | 10/1998 | Massie et al. | |
| 6,065,837 A | 5/2000 | Goldfain et al. | |
| 6,092,898 A | 7/2000 | De Juan, Jr. | |
| 6,267,752 B1 | 7/2001 | Svetliza | |
| 6,296,358 B1 | 10/2001 | Cornsweet et al. | |
| 6,305,804 B1 | 10/2001 | Rice et al. | |
| 6,361,167 B1 | 3/2002 | Su et al. | |
| 6,409,341 B1 | 6/2002 | Goldfain et al. | |
| 6,446,795 B1 | 9/2002 | Allen et al. | |
| 6,636,696 B2 | 10/2003 | Saito | |
| 6,685,317 B2 | 2/2004 | Su et al. | |
| 6,761,455 B2 * | 7/2004 | Sumiya | A61B 3/156 351/221 |
| 6,801,913 B2 | 10/2004 | Matsumura et al. | |
| 7,025,459 B2 | 4/2006 | Cornsweet et al. | |
| 7,048,379 B2 * | 5/2006 | Miller | A61B 3/156 351/205 |
| 7,147,329 B2 | 12/2006 | Stone et al. | |
| 7,156,518 B2 * | 1/2007 | Cornsweet | A61B 3/10 351/205 |
| 7,261,416 B2 | 8/2007 | Nishio et al. | |
| 7,306,336 B2 | 12/2007 | Akita et al. | |
| 7,347,553 B2 | 3/2008 | Matsumoto | |
| 7,357,248 B2 | 4/2008 | Sivakumar et al. | |
| 7,360,895 B2 | 4/2008 | Cornsweet et al. | |
| 7,387,385 B2 | 6/2008 | Sander | |
| 7,445,335 B2 | 11/2008 | Su et al. | |
| 7,448,753 B1 | 11/2008 | Chinnock | |
| 7,465,049 B2 * | 12/2008 | Maeda | A61B 3/1208 351/205 |
| 7,499,634 B2 | 3/2009 | Yogesan et al. | |
| 7,508,524 B2 | 3/2009 | Mahadevan-Jansen et al. | |
| 7,568,802 B2 | 8/2009 | Phinney et al. | |
| 7,621,636 B2 | 11/2009 | Su et al. | |
| 7,621,638 B2 | 11/2009 | Su et al. | |
| 7,650,064 B2 | 1/2010 | Isogai et al. | |
| 7,677,730 B2 | 3/2010 | Shimizu | |
| 7,731,361 B2 | 6/2010 | Honda | |
| 7,802,884 B2 * | 9/2010 | Feldon | A61B 3/1208 351/206 |
| 7,815,310 B2 | 10/2010 | Su et al. | |
| 7,824,035 B2 | 11/2010 | Yamada et al. | |
| 7,854,510 B2 | 12/2010 | Verdooner et al. | |
| 7,986,859 B2 | 7/2011 | Fischer | |
| 8,002,410 B2 | 8/2011 | Shea | |
| 8,011,504 B1 | 9/2011 | Farberov et al. | |
| 8,049,899 B2 | 11/2011 | Waelti et al. | |
| 8,064,989 B2 | 11/2011 | Brown et al. | |
| 8,103,061 B2 | 1/2012 | Payonk et al. | |
| 8,111,874 B2 | 2/2012 | Chan | |
| 8,115,830 B2 | 2/2012 | Kato et al. | |
| 8,118,431 B2 | 2/2012 | Shea et al. | |
| 8,237,805 B2 | 8/2012 | Nozaki | |
| 8,313,195 B2 | 11/2012 | Itoh et al. | |
| 8,328,356 B2 | 12/2012 | Cheng et al. | |
| 8,330,808 B2 | 12/2012 | Satake | |
| 8,356,900 B2 | 1/2013 | Zhou et al. | |
| 8,368,771 B2 | 2/2013 | Kino | |
| 8,421,855 B2 | 4/2013 | Buckland et al. | |
| 8,449,112 B2 | 5/2013 | Kishida | |
| 8,449,115 B2 | 5/2013 | Aikawa et al. | |
| 8,459,794 B2 | 6/2013 | Juhasz et al. | |
| 8,480,232 B2 | 7/2013 | Aikawa | |
| 8,506,082 B2 | 8/2013 | Saito | |
| 8,506,083 B2 | 8/2013 | Zhou et al. | |
| 8,518,109 B2 | 8/2013 | Shea et al. | |
| 8,562,135 B2 * | 10/2013 | Endo | A61B 3/1035 351/205 |
| 8,594,757 B2 | 11/2013 | Boppart et al. | |
| 8,777,413 B2 | 7/2014 | Zhou et al. | |
| 8,811,745 B2 | 8/2014 | Farsiu et al. | |
| 8,820,929 B2 | 9/2014 | Shea et al. | |
| 8,820,931 B2 | 9/2014 | Walsh et al. | |
| 8,860,796 B2 | 10/2014 | Buckland et al. | |
| 8,861,061 B1 | 10/2014 | Graham et al. | |
| 8,896,842 B2 | 11/2014 | Bower et al. | |
| 8,926,350 B2 | 1/2015 | Wolfe et al. | |
| 8,955,971 B2 | 2/2015 | Ichikawa et al. | |
| 8,967,807 B2 | 3/2015 | Mizuno | |
| 9,022,569 B2 | 5/2015 | Nakahara et al. | |
| 9,106,831 B2 | 8/2015 | Miyamoto et al. | |
| 9,119,563 B2 | 9/2015 | Buckland et al. | |
| 9,149,179 B2 | 10/2015 | Barnard et al. | |
| 9,171,351 B2 | 10/2015 | Kita | |
| 2002/0097379 A1 | 7/2002 | Goldfain et al. | |
| 2003/0174211 A1 | 9/2003 | Imaoka et al. | |
| 2004/0118431 A1 | 6/2004 | Flynn | |
| 2005/0018135 A1 | 1/2005 | Maeda et al. | |
| 2005/0270484 A1 | 12/2005 | Maeda et al. | |
| 2005/0284774 A1 | 12/2005 | Mordaunt | |
| 2006/0114411 A1 | 6/2006 | Wei et al. | |
| 2006/0176447 A1 | 8/2006 | Reis | |
| 2006/0257138 A1 | 11/2006 | Fromm | |
| 2007/0236663 A1 | 10/2007 | Waldorf et al. | |
| 2007/0244393 A1 | 10/2007 | Oshiki et al. | |
| 2008/0033371 A1 | 2/2008 | Updegraff et al. | |
| 2008/0071254 A1 | 3/2008 | Lummis et al. | |
| 2008/0211420 A1 | 9/2008 | Walker et al. | |
| 2009/0141237 A1 | 6/2009 | Izatt et al. | |
| 2009/0153797 A1 | 6/2009 | Allon et al. | |
| 2009/0185135 A1 | 7/2009 | Volk | |
| 2009/0211586 A1 | 8/2009 | Shea et al. | |
| 2010/0091244 A1 | 4/2010 | Volk | |
| 2010/0118270 A1 | 5/2010 | Shea et al. | |
| 2010/0149490 A1 | 6/2010 | Olivier et al. | |
| 2010/0184479 A1 | 7/2010 | Griffin | |
| 2010/0201604 A1 | 8/2010 | Kee et al. | |
| 2010/0228236 A1 | 9/2010 | Muhlhoff et al. | |
| 2010/0278394 A1 * | 11/2010 | Raguin | G06K 9/00604 382/117 |
| 2011/0051086 A1 | 3/2011 | Takai et al. | |
| 2011/0052205 A1 | 3/2011 | Yu et al. | |
| 2011/0085137 A1 | 4/2011 | Kleen et al. | |
| 2011/0090460 A1 | 4/2011 | Graham et al. | |
| 2011/0103655 A1 | 5/2011 | Young et al. | |
| 2011/0176109 A1 | 7/2011 | Mann | |
| 2011/0267583 A1 | 11/2011 | Hayashi | |
| 2011/0299036 A1 | 12/2011 | Goldenholz | |
| 2012/0026461 A1 | 2/2012 | Chou et al. | |
| 2012/0050683 A1 | 3/2012 | Yates | |
| 2012/0092619 A1 * | 4/2012 | Rowe | A61B 3/0016 351/221 |
| 2012/0099077 A1 | 4/2012 | Abt | |
| 2012/0138503 A1 | 6/2012 | Patel | |
| 2012/0162602 A1 | 6/2012 | Huening et al. | |
| 2012/0224142 A1 | 9/2012 | Cornsweet et al. | |
| 2012/0229617 A1 | 9/2012 | Yates et al. | |
| 2012/0249748 A1 | 10/2012 | Nagano | |
| 2012/0274900 A1 | 11/2012 | Horn et al. | |
| 2012/0287255 A1 * | 11/2012 | Ignatovich | A61B 3/1208 348/78 |
| 2012/0300998 A1 | 11/2012 | Loudovski et al. | |
| 2012/0320583 A1 | 12/2012 | Van Bommel et al. | |
| 2013/0033593 A1 | 2/2013 | Chinnock et al. | |
| 2013/0044200 A1 | 2/2013 | Brill et al. | |
| 2013/0057828 A1 | 3/2013 | De Smet | |
| 2013/0103014 A1 * | 4/2013 | Gooding | A61B 3/102 606/6 |

(56) References Cited

U.S. PATENT DOCUMENTS

| | | | |
|---|---|---|---|
| 2013/0135584 A1* | 5/2013 | Alasaarela | A61B 3/1208 351/206 |
| 2013/0182895 A1 | 7/2013 | Touzov et al. | |
| 2013/0235345 A1 | 9/2013 | Ohban | |
| 2013/0261610 A1 | 10/2013 | LaConte et al. | |
| 2013/0301003 A1 | 11/2013 | Wells et al. | |
| 2013/0321906 A1 | 12/2013 | Kriofske et al. | |
| 2014/0055749 A1 | 2/2014 | Zhou et al. | |
| 2014/0063455 A1 | 3/2014 | Zhou et al. | |
| 2014/0063456 A1 | 3/2014 | Zhou et al. | |
| 2014/0063457 A1 | 3/2014 | Zhou et al. | |
| 2014/0063459 A1 | 3/2014 | Zhou et al. | |
| 2014/0063462 A1 | 3/2014 | Zhou et al. | |
| 2014/0063463 A1 | 3/2014 | Zhou et al. | |
| 2014/0078467 A1 | 3/2014 | Su | |
| 2014/0085603 A1* | 3/2014 | Su | A61B 3/145 351/206 |
| 2014/0111768 A1 | 4/2014 | Komine | |
| 2014/0125949 A1 | 5/2014 | Shea et al. | |
| 2014/0221826 A1 | 8/2014 | Joos et al. | |
| 2014/0226128 A1 | 8/2014 | Lawson et al. | |
| 2014/0293033 A1 | 10/2014 | Takii | |
| 2014/0307226 A1 | 10/2014 | Lathrop et al. | |
| 2014/0347628 A1 | 11/2014 | Martinez Corral et al. | |
| 2014/0375952 A1 | 12/2014 | Hanebuchi | |
| 2015/0146170 A1 | 5/2015 | Su | |
| 2016/0007850 A1 | 1/2016 | Su | |
| 2016/0029887 A1 | 2/2016 | Su | |
| 2016/0073877 A1 | 3/2016 | Su et al. | |
| 2016/0073878 A1 | 3/2016 | Su et al. | |
| 2016/0213250 A1 | 7/2016 | Su | |

FOREIGN PATENT DOCUMENTS

| | | | | |
|---|---|---|---|---|
| EP | 1289407 B1 | 12/2009 | | |
| EP | 2164383 A2 | 3/2010 | | |
| EP | 1928297 B1 | 11/2010 | | |
| EP | 2296531 A1 | 3/2011 | | |
| EP | 2312994 A2 | 4/2011 | | |
| EP | 2334222 A2 | 6/2011 | | |
| EP | 2066226 B1 | 12/2012 | | |
| EP | 2790570 A1 | 10/2014 | | |
| EP | 2845534 A1 | 3/2015 | | |
| FI | WO 2012038587 A1 * | 3/2012 | | A61B 3/1208 |
| JP | 2002238853 A | 8/2002 | | |
| SG | WO 2013162471 A2 * | 10/2013 | | A61B 3/1208 |
| TW | 201204314 A1 | 2/2012 | | |
| WO | WO03/057024 A1 | 7/2003 | | |
| WO | WO2006/013579 A1 | 2/2006 | | |
| WO | WO2010009450 A1 | 1/2010 | | |
| WO | WO2010/096756 A1 | 8/2010 | | |
| WO | WO2010/108228 A1 | 9/2010 | | |
| WO | WO2010117386 A1 | 10/2010 | | |
| WO | WO2011/022803 A1 | 3/2011 | | |
| WO | WO 2011069137 A1 * | 6/2011 | | A61B 3/1208 |
| WO | WO2012018991 A2 | 2/2012 | | |
| WO | WO2012/118907 A2 | 9/2012 | | |
| WO | WO2012118962 A2 | 9/2012 | | |
| WO | WO2012/154278 A1 | 11/2012 | | |
| WO | WO2013/020092 A1 | 2/2013 | | |
| WO | WO2013/059678 A1 | 4/2013 | | |
| WO | WO 2013162471 A1 * | 10/2013 | | |
| WO | WO 2013162471 A2 * | 10/2013 | | |
| WO | WO2013/165689 A1 | 11/2013 | | |
| WO | WO2013165614 A1 | 11/2013 | | |
| WO | WO2014/074573 A1 | 5/2014 | | |

OTHER PUBLICATIONS

Haddock, D. et al. "Simple, Inexpensive Technique for High-Quality Smartphone Fundus Photography in Human and Animal Eyes." Journal of Ophthalmology (2013).*

Su et al.; U.S. Appl. No. 14/220,005 entitled "Eye Imaging Apparatus and Systems," filed Mar. 19, 2014.

Su, Wei; U.S. Appl. No. 14/191,291 entitled "Eye Imaging Apparatus with a Wide Field of View and Related Methods," filed Feb. 26, 2014.

Su et al.; U.S. Appl. No. 14/312,590 entitled "Mechanical Features of an Eye Imaging Apparatus," filed Jun. 23, 2014.

American Academy of Ophthalmology; Vision Screening for Infants and Children (Policy Statement); American Association for Pediatric Ophthalmology and Strabismus; 3 pgs; © 2013 (earliest approval date: May 1991).

Device Optical; Kowa Genesis-D Hand Held Retinal Camera (product information); 3 pgs.; retrieved Jun. 23, 2014 from the internet (http://www.deviceoptical.com/pd_kowa_genesisd.cfm).

Freebody; Reduced to the essentials—portable imaging gets high-tech; BioPhotonics; 13 pages; retrieved Jul. 13, 2016 from the internet at (http://www.photonics.com/Article.aspx?PID=1&VID=127&IID=847&AID=57816).

Izatt et al.; Theory of optical coherence tomography; Optical Coherence Tomography; Springer berlin Heidelberg; pp. 47-72; (year of pub. sufficiently earlier than effective US filing date and any foreign priority date); 2008.

Pavlis et al.; Optical differences between telescopes and microscopes; 5 pages; retrieved Jul. 13, 2016 from the internet at (http://www.microscopy-uk.org.uk/mag/imgjan10/mik-tele.pdf).

Ruggeri et al.; Imaging and full-length biometry of the eye during accommodation using spectral domain OCT with an optical switch, Biomedical Optics Express, 3(7); pp. 1506-1520; Jul. 6, 2012.

Su et al.; U.S. Appl. No. 15/144,679 entitled "Eye imaging apparatus and systems," filed May 2, 2016.

Su; U.S. Appl. No. 15/186,402 entitled "Wide field of view optical coherence tomography imaging system," filed Jun. 17, 2016.

* cited by examiner

PORTABLE EYE IMAGING APPARATUS

CROSS-REFERENCE TO RELATED APPLICATION

This application claims priority under 35 U.S.C. §119(e) to U.S. Provisional Patent Application No. 61/593,865, filed Feb. 2, 2012.

BACKGROUND OF THE INVENTION

Various portable imaging systems have been proposed to image the posterior of human eyes (fundus camera) over the years. Some of the cameras are designed with the front of their objective lens contacting the cornea of the patients, while others are for non-contact operation. The contact type of fundus cameras exhibits the advantage of having much wider field of view and with easier alignment for operator. Certainly the required extra effort in sterilization and discomfort to patients are the clear short comes of this type of camera. Due to the unique optical path for projecting light through the opening of the iris and crystal lens of the eye, the image quality, in terms of contrast and color saturation, of wide field fundus camera is often inferior to that from narrow field non-contact cameras. In particular, the images often exhibit a layer of strong haziness due to the scattering of illumination light against the retina in background for patients with dark pigmentation in the eyes. In the prior art, a portable contact type of fundus camera is proposed where the hand held imaging capturing unit is separated from the light source and the rest of bulky electronics. An optical cable is used to transmit light from light source into the hand held unit, while the captured images are sent to the computer through an electrical cable. A movable cart is proposed to house the light source, computer, monitor, printer and power conditioner, etc. However, from the user's perspective, the use of the heavy cables makes precision adjustment of camera and handling of the imaging unit rather difficult. The heavy weight of the cart carrying the computer and all of accessories also makes the system difficult to move from within the hospitals, and almost impossible to transport between hospitals.

The need for a portable digital imaging device, which utilizes the advanced features of wireless data transmission and high computing power of mobile computing devices, is generating interest for the next generation of medical imaging devices. Such portable and wireless imaging devices will use miniature cameras and solid state lighting technology to achieve the significant reduction in size while maintain the performance against the desk-top type of imaging systems.

DETAILED DESCRIPTION OF PREFERRED EMBODIMENTS

Figure 1:
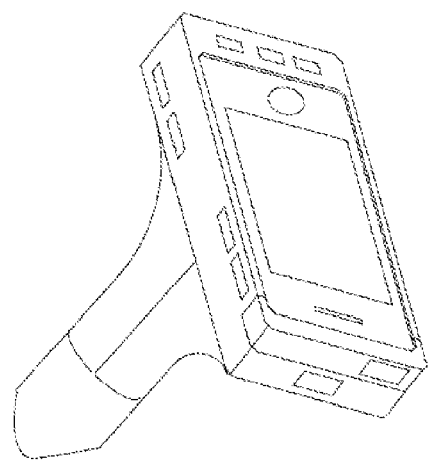
FIG. 1 is the embodiment for the exterior of the portable eye imaging apparatus with a touchscreen display mounted on the top of the camera body.

The proposed portable imaging apparatus, as shown in FIG. 1, is designed to be carried by the users in a small suite case or in other convenient manners due to its compactness, to be powered by its battery for rather long lasting operation and to be easy at use by people with the minimum training. It is designed to be operated by grabbing the cylindrical part of the body with one hand, while using another hand to manipulate the computing/display interfaces. The users could also precisely adjust the position/angle of the apparatus with one hand and free another hand to work on other tasks, for example, opening the eyelids of the patient with fingers. The captured images could be transferred to other devices or internet based devices, like storage unit, through wired or wireless means. In its medical applications, it could be used as a diseases screening or medical diagnosis device for the ophthalmic applications, or portable medical imaging device for other medical needs, i.e., ENT or dermatology. Portion of its imaging and lighting optics are designed to be removable or replaceable with other optics. When the portion of optics for imaging and lighting is replaced or removed, its potential use or applications could be significantly expanded. For example, used as an ophthalmic imaging device, the apparatus could be used to take images of posterior portion of the eye with various magnifications and under the illumination from broadband or narrow spectral light source. The iris of the patient may or may not need to be dilated with special drugs. The imaging apparatus also could be used to image the anterior of the eye with or without additional optics, with its own lighting or extra external light source(s). It could provide stereoscopic (3D) color imaging capability for the anterior portion of eye with illumination from an integrated solid state lighting apparatus, which could then be viewed in stereoscopic (3D) fashion later when a proper display device (3D) is used. The color fundus images from the posterior of eye could be obtained, in the form of either mono (2D) or stereoscopic (3D). Such imaging apparatus could have applications in the areas other than medical, for example, in the security screening applications where the images from the posterior/anterior of the eye could be used for personal identification purpose.

It is also important to point out that such contact eye imaging apparatus could also be used to image the eyes from other than that of human. For example, it could be used, with or without modification of optics from its human use, to image the eyes of horses, cat, dog, rabbit, etc.

Figure 2:
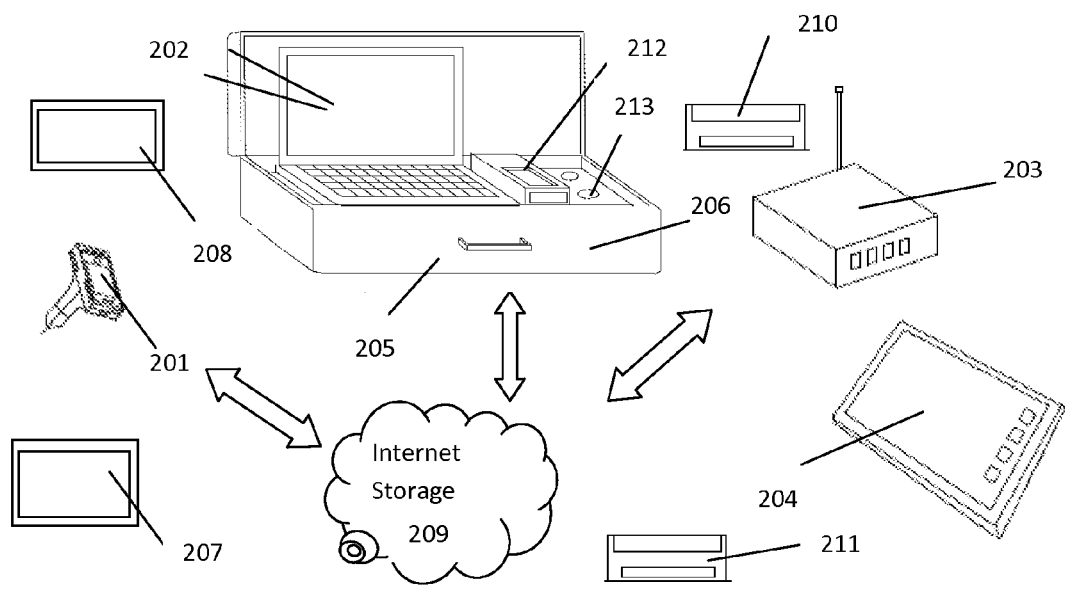
FIG. 2 is the schematic of a preferred medical imaging system which includes the portable eye imaging apparatus and all of supporting accessories.

The imaging apparatus shown in FIG. 1 could be used in a medical system described in FIG. 2, where the images and patient information are captured, input and stored, and later to be shared and reviewed by different medical professionals at same or different locations. The medical system consists of four main components, including imaging apparatus 201 (ICU), image computing apparatus 202 (IU), image storage apparatus 203 and separate image reviewing apparatus 204. Each component would have its own power supply/battery, although the battery could be charged automatically when they are connected to each other. For example, the battery in the apparatus 201 could be automatically recharged by the larger battery in apparatus 202 when it is placed inside the carry-on suitcase 205 and/or connected through a USB cable. The recharging process would be stopped when the battery reaches its full capacity. The imaging apparatus 201 and the computing apparatus 202 could be stored in a suitcase 205 and to be carried away by the users. The suitcase 205 could contain a power supply, which could be hooked up with the external power source, and the extra battery 206. The extra battery 206 could be placed under the bottom of the suitcase, and is used to charge the batteries in the imaging apparatus 201 and the image computing apparatus 202 when they are placed in the suitcase or connected with the battery. The larger capacity of the extra battery 206 enables the imaging system to be operated in long period of time without the need to access to the external power sources. The images captured in the imaging apparatus 201 could be temporarily stored in its own memory, or immediately be transferred to the image computing apparatus 202, via wired or wireless means, although the wireless means like WiFi or Bluetooth etc., are the preferred means. The transmission of images from the apparatus 201 to 202 could be in the form of still images or live video images with or without using the real time image compression algorithm/process. In the case where the live video is transmitted, the live images captured on apparatus 201 could be viewed on the screen of the apparatus 202 in real-time, and also possibly on one or multiple external monitor/screen of even larger size which receive the video signal from the apparatus 202. The image/data received from the apparatus 201 could be processed in the apparatus 202 to improve the quality/performance, and then be displayed on screen or recorded in its own storage device, together with other related information of the patients. As the result, the users could capture the images with smaller imaging apparatus, 201, while viewing the live video at larger screen from the apparatus 202, or multiple devices, 207 and 208, through wire or wireless connections. The larger screen or screens could also be viewed by a larger group of people at the more convenient locations. The data transmission between the apparatus 201 and 202 is bidirectional, for example, allows patient ID to be passed from apparatus 202 to 201 and synchronized. The recording of the images in the apparatus 202 includes the still images and video clips depending on the need of the users. The video and still images could share same format/resolution or have different resolutions. The data/image recording on the apparatus 202 is stored in a unique data base which identifies with the imaging apparatus 201, and is supposed to be temporary in nature. The more permanent storage of patient data/images is carried out in the image storage apparatus 203, which often is placed in a secured location for the safety of data. The data exchange/synchronization between the apparatus 202 and 203 could be carried out through the wired or wireless means, when the two units are placed in close proximity. The storage device in the apparatus 203 has extra large capacity and redundancy to protect the data, and with data base to store data from either a single apparatus 202 or multiple of apparatus 202. The image reviewing apparatus 204 could be a simple display device attached to the apparatus 203, or a detachable computing device connected with the apparatus 203 through the wired or wireless means. In case a detachable device with wireless connection, for example a tablet PC, the users could use multiple of apparatus 204 to review the patient information and images at a distance from the apparatus 203. It is important to point out that the image capturing apparatus 201 could be used to store the images, both still and video clips, while broadcast the video/live images to multiple display devices 207 and 208 directly without the use of the apparatus 202. Also users could also operate the apparatus 201 without the apparatus 202, then directly transfer the images to the apparatus 203 for safe storage. In the situation where the network storage 209 is used, instead using the local storage, the images from the apparatus 201, 202 could be directly transmitted out through the wired or wireless connection to the network. Such data transmission is also bi-directional, meaning that the data from the network storage 209 could also be down loaded to and to be synchronized with the apparatus 201 or 202. It is also obvious that the images and patient information stored in apparatus 203 could be synchronized with the database in the network storage 209 so that they could be shared in an even larger patient pool. The color images from the database in the apparatus 201, 202 or 203 could be printed out from a color printer 210, while the patient information in the apparatus 201, 202, or 203 with or without color images could be printed out from a report printer 211 of larger format. The connection between the printers 210, 211 and the apparatus 201, 202, and 203 could be through the wired or wireless means. The printer 210 and 211 could be stand-alone printers, as shown in FIG. 2. However, one additional color printer 212, just as printer 210, could be placed in the suitcase 205 for printing color photos at convenience. Extra storage space 213 is also provided in the suitcase 205 for additional optional optics and other accessories.

Figure 2A:
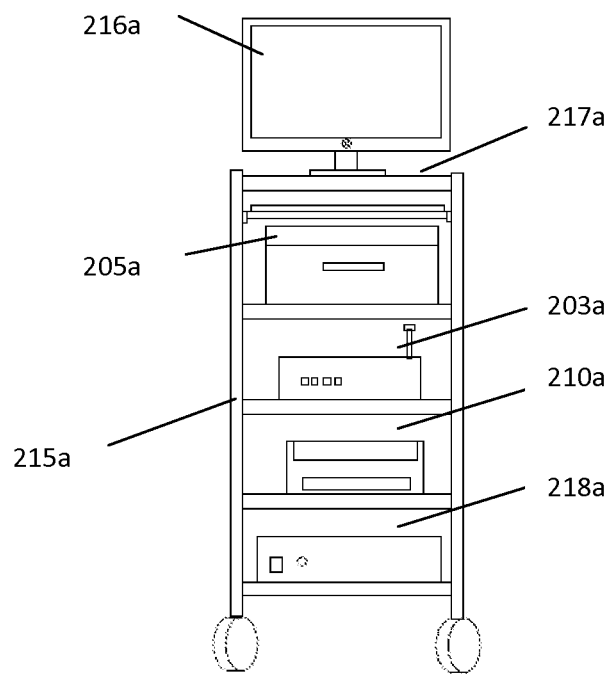
FIG. 2a is one embodiment of the medical imaging system where the whole system is placed on a mobile cart.

The setup and arrangement of the described imaging apparatus/storage devices could also take other forms. One example is shown in FIG. 2a, in which the key components of an imaging system is placed on a mobile cart, for the convenience of being used in the clinic and surgical rooms. As shown in FIG. 2a, the cart 215a is built with multiple shelves and wheels in order to store multiple components and allow easy maneuver in the tight space. Same as the suitcase 205 in FIG. 2, the portable carry on suitcase 205*a* could be placed on one of shelves and with the imaging apparatus stored inside. The user could take out the entire suitcase 205*a* from the cart and use it in other locations, or use the suitcase purely as the storage box in the cart. In other words, the computing unit 202 and extra battery 206, shown in FIG. 2, are included in the suitcase 205*a* and are used in same manner as described in the previous paragraphs. When the suitcase 205*a* is placed on the shelf, its power cord could be hooked up directly into the electric power supply system of the cart; and its battery be recharged automatically. The monitor 216*a*, functioned as the display 207 shown in FIG. 2, is used to display both live and still images, including the patient information. The monitor 216*a* could also be a display of another computing device similar to the computing unit 202 in FIG. 2. An information input device 217*a* is placed on the self to allow the users to input the patient information into and navigate through the computing device. The device 217*a* could be a key board connecting the computing device 216*a* or the computing unit 202, or even the touch screening of another computing device. The connection or information exchange between the device 217*a*, device 216*a* and 202 could be through the wires or wireless means. The information storage unit 203*a* functions in same or similar manner as the unit 203 in FIG. 2, and is used to store the patient information and images more permanently. The printing device 210*a* is used to print out color images, or even medical report at the site. The device 210*a* could be just one printer or multiple printers depending on the needs. A power conditioning unit 218*a* is used to supply electric power to the whole system on the cart as required by the medical regulations, and to provide undisrupted power supply to the whole system when the cart is disconnected from the electric main power.

Figure 3:
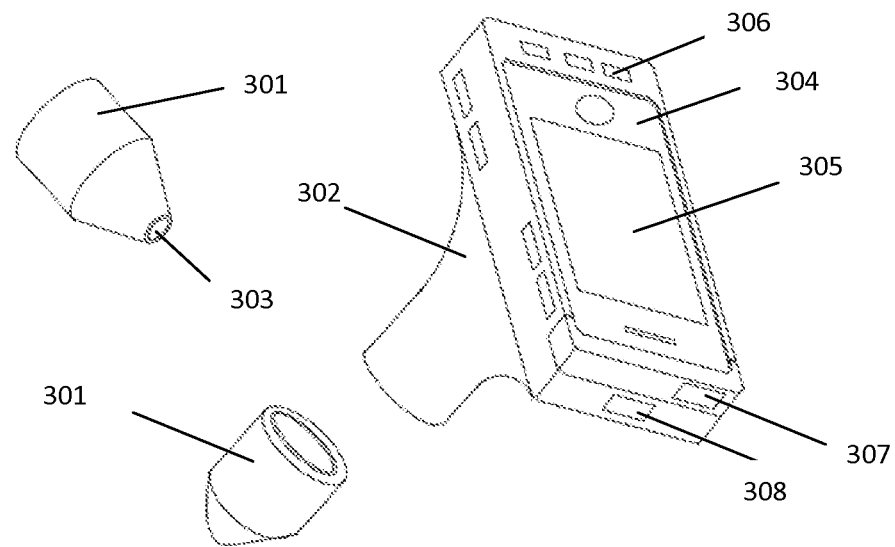
FIG. 3 provides details of the portable eye imaging apparatus which consists of the posterior eye imaging subsystem and the computing/communication subsystem.

More details of the portable imaging apparatus described in this application is provide in FIG. 3, which is constructed with two main subsystems: the removable posterior eye imaging subsystem 301 and the portable computing/communication subsystem 302. The described portable imaging apparatus is capable of imaging both posterior and anterior portion of the eye, with same and/or different optical system(s) and digital image capturing system(s). To photograph the posterior of the eye, the front portion of the removable posterior eye imaging subsystem 301 should be placed over the cornea of the eye with light touch. The optical window 303 of the front portion 301 is designed to have a curvature approximately match radius of the eye cornea. An optical index matching liquid or gel could be added between the cornea and the front optics to reduce the light scattering and the optical aberrations for the imaging system. The illumination light is projected from the front optical window 303 and through the designated area on the cornea and the crystalline lens of the eye, and eventually onto the posterior of the eye. The image of the posterior of eye, from retina to the posterior vitreous chamber of the eye, is then relayed by the optics within and behind the optical window 303, and finally is formed onto a secondary image plane. The secondary image plane could be designed to either be located within the posterior eye imaging subsystem 301 or the computing/communication subsystem 302. A second group of relay optics is then added to relay the image from the secondary image plane onto the electronic image sensor which is located inside the computing/communication subsystem 302. The electronic image sensor is capable of taking both the stream of real-time video images and the high resolution still images, through the pre-programmed functions. The electronic image sensor could be either CCD or CMOS, and other type of digital cameras. The images from the electronic image sensor is then processed by the processor in the computing/communication subsystem 302, and ready to be transmitted out of the portable imaging apparatus through the wired or wireless means.

As shown in FIG. 3, the computing/communication subsystem 302 consists of a modified version of a smart phone or similar portable computing device 304 with the built-in data communication capability. Preferably the data from the image sensor could be input into the portable computing device 304 through the standard portal or special data bus built for such cameras. In case that a standard version of such computing device is used, the camera could also be connected electrically with the computing device 304 through its standard connection I/O port, for example, like the USB or HDMI port. The computing device 304 is encapsulated inside the body of the computing/communication apparatus 302, with only the display screen 305, which employs the touch screen control features, and some of control buttons 306 exposed or made operational through the mechanical relay mechanism 307. The portable computing/communication subsystem, 302, is capable of capturing the data from multiple imaging cameras, in real time and sequentially or simultaneously, and then displaying the live images on its screen, 305. The cameras and its image capturing features could be controlled through the functions of the device on the touch screen, 305, or other functional buttons, like 306, on the computing/communication subsystem 302, or even by the voice command functions of the device 304. The screen 305 could display either simple mono images or stereoscopic (3D) images. The portable computing/communication subsystem, 302, is also able to exchange data and communicate with other, electronics devices through the wired or wireless means, like WiFi or 3G standard telecommunication protocols.

The recharge of the batteries used in the portable imaging apparatus shown in FIG. 3 could be performed through the standard USB port or other built-in recharging port. However, in order to keep the whole device water sealed, the existence of such electric port could be problematic. One solution could be the use of power charging device without the use of cable, in which the power receiver module is built into the body of the computing/communication apparatus 302 near its side surfaces. When the apparatus 302 is placed next to the power charging mat or pad, its batteries could be charged through the exchange of power from the power mat without using the connection cable.

During the process of the posterior imaging, the optical focusing mechanism could be set to either manual or automatic. In the fully automatic mode, the portable imaging apparatus automatically look for features in the images and try to adjust the optical focus mechanism to achieve the best focus. In the manual mode, the users could pick up the area of focus over the live images by using the touch screen input 305 of the portable computing device. The apparatus would adjust the optical focus mechanism to achieve the best focus in that area and then provide a visual or audible indication when it is in focus. The image brightness or exposure could also be controlled through either automatic or manual mode. In the automatic exposure mode, the users could either allow apparatus to adjust the brightness of the images fully automatically based on the preset imaging criteria, or fine tune the exposure by selecting an area in the image for proper exposure which often is also the area for fine focus adjustment. In either case, the overall brightness of the image could be adjusted or set by the users according to their preference. There are two ways to control the brightness of the image, the sensitivity of image sensor or luminance of the lighting. When the quality of the images or the noise level of the image is a critical measure, the sensitivity of the image sensor is often set to a fixed level. Then the luminance of the lighting from the solid state lighting device is adjusted to achieve the desired brightness automatically. Certainly, a maximum level of allowable luminance is set in the apparatus in order to prevent it to exceed the level allowed by regulations due to concern for phototoxicity to the eye. If the level of light exposure is more important, then the level of the luminance from the light source could be fixed or selected by the users, while the sensitivity of the image sensor is adjusted automatically in the second approach.

The computing/communication apparatus provides a platform for integrating more functional modules and features into the portable image apparatus shown in FIG. 3, beyond the optical imaging application described in the previous paragraphs. When the module 301 is connected with the module 302, the electrical connection could also be provided between two modules to power the electronic devices in the module 301 and to send electronic signals back to module 302. One embodiment of this invention is to replace the module 301 with an ultrasound probe which has similar profile and size as the optical imaging subsystem discussed above. The ultrasound probe could be an A-scan or B-scan type of probe used to measure the size and structure of the same eye. Both types of probes have an ultrasound wand (transducer) similar to that of the optical window 303 shown FIG. 3, which are placed against either cornea or eyelids during the tests. Same type of liquid or gel for the optical imaging is used between the probe and tissue. The ultrasound transducer generates the high-frequency sound waves that travel through the eye, and also picks up the reflections (echoes) of the sound waves to form a picture of the structure of the eye. The measurement from the A-Scan probe provides the structural information on the length of the eye, while that from the B-scan ultrasonography provides cross sectional two-dimensional images of the inner eye. The data from the probe could be preprocessed by the electronics circuits housed in the module 302 before it is sent to portable computing device 304. The result could then be displayed on the touch screen 305 for the users, or transmitted wirelessly to other computing/display devices as demonstrated in FIG. 2.

It is not necessary to build the posterior imaging apparatus 301 and the computing/communication subsystem 302 in two separate units. In one embodiment of the eye imaging apparatus, the optics in subsystem 301 and 302 are built into one shell with front section permanently fixed with the rest of apparatus body.

Figure 4:
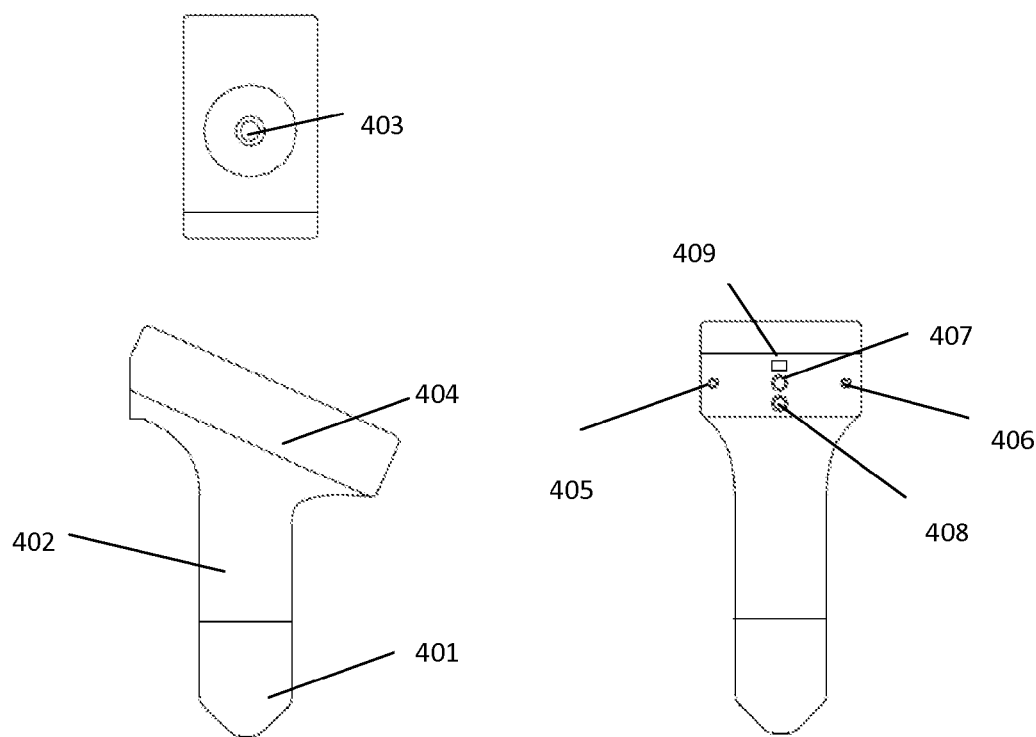
FIG. 4 shows an embodiment of the independent exterior imaging subsystem which is mounted on the shell of the portable eye imaging apparatus.

Through the posterior eye imaging subsystem, as shown in FIG. 3, the portable imaging apparatus not only could be used to photograph the posterior of eye, it could also to be used to photograph the exterior of eye or the exterior of other subjects, when the proper adjustment for focus is made. However, to achieve better image quality and utilize special lighting for the subject, a more sophisticated exterior lighting/imaging subsystem could be built into the portable imaging apparatus. FIG. 4 shows more details of the exterior of the portable imaging apparatus, where an exterior imaging/lighting subsystem is built on the exterior of the eye imaging apparatus. Here, the portable computing device 404 (same as 304 in FIG. 3) is mounted on top of the computing/communication subsystem 402 while the posterior imaging subsystem 401 is mounted at another side with its imaging window 403 at the bottom. The device 404 is mounted at an inclined angle, shown in FIG. 4, for allowing easier operation of the device 404 by the users. However, the device 404 could also be mounted on the top with its viewing screen simply normal to the optical axis of the posterior imaging subsystem. In one indication shown in FIG. 4, the exterior imaging/lighting subsystem consists of two solid state lighting units 405, 406 and one miniature camera (with imaging optics) 407 between them. The solid state lighting units 405 and 406 consist of the light emitting diodes and possibly the light conditioning optics in the front. The diodes in 405 and 406 could either emit light with narrow spectral bandwidth and in visible or invisible, like UV or IR, spectrum. The units 405 and 406 could also emit light in broad spectral bandwidth, like white light to human eyes. Accordingly, the camera 407 could also work in either the visible light spectrum or invisible spectrum. Two additional lighting units 408 and 409 are also mounted next to the camera 407, and with different lighting purposes. The lighting unit 408 would use a solid state emitter with light in the broadband spectrum (white light) and visible to human eye. The light from unit 409 could be either with narrow or broad band spectrum, or in either visible or invisible spectrum to human eyes. For the control, the light from lighting unit 405, 406, 408 and 409 could be turned on at same time, in different combinations or individually. The imaging optics in the front of camera 407 comes with the focusing adjustment capability to allow high quality imaging at different distances. The optics could also employ the optical zooming capability to allow the users to change the magnification of the images for the desired object at a fixed distance.

Figure 5:
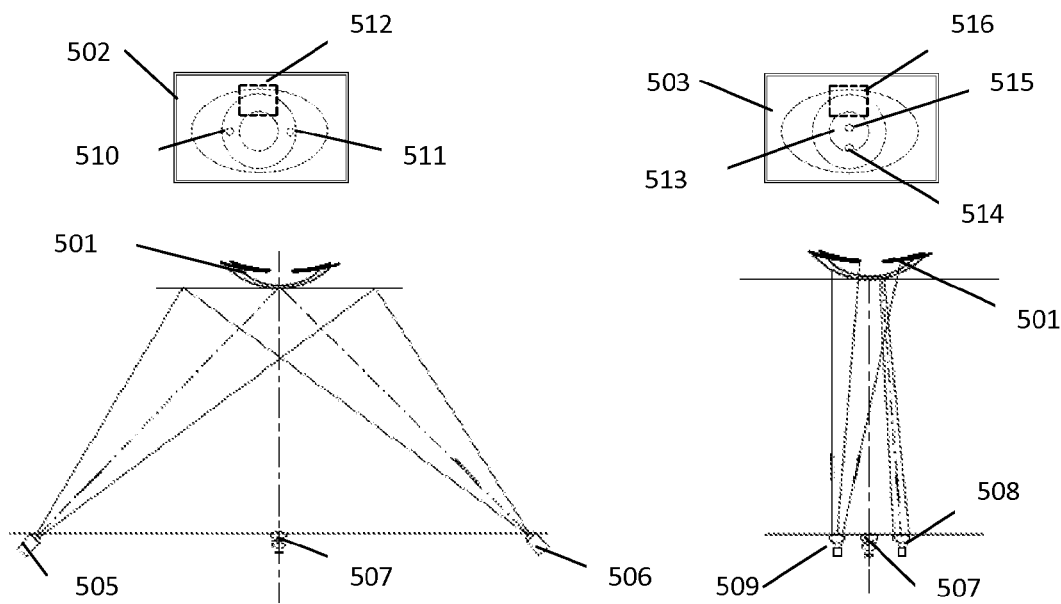
FIG. 5 shows the schematics of the special lighting system for the exterior imaging subsystem which enables imaging of the exterior of eyes and other organs of the human.

A side view of the exterior imaging subsystem is shown in FIGS. 5, where lighting units 505, 506, 508, 509 are same of 405, 406, 408, 409 shown in FIG. 4 respectively. The camera 407 in FIG. 4, with more details, is shown as 507 in FIG. 5. The light emitting diodes and the light conditioning optics of the lighting units 405 and 406 are arranged to project the diverging light with center of their cones converged at the optical axis of the imaging camera 507. In the FIG. 5, the object 501, which is an eye, is located at the convergent point of lighting and is seen in the center of the picture 502 and 503 taken from the camera 507. The intensity or brightness of the light from the lighting unit 505 and 506 are adjustable, either manually or automatically, and to be seen with same or different brightness in the images of camera 507. Two bright spots 510 and 511 could be seen in the picture 502 from the spectacular reflection of light off the cornea. The purpose of such optical lighting arrangement is to allow uniform illumination of the object when both lighting unit 505 and 506 are turned on, and to produce high contrast images when only one lighting unit is turned on. The contrast of the images (through the lighting) could be adjusted by the ratio of the light intensity from two lighting units 505 and 506. The default setting could be that of identical brightness for 505 and 506, while the brightness is adjustable collectively. The camera 507 is equipped with a focusing sensor which detects the focus status within a specific area indicated to the users within the live image window. In FIG. 5, a small color block 512 is shown in the picture 502, which indicates the area of focusing zone. The users could select or change the area of focus by taping the desired area in the window of live images shown the touch screen of the portable computing device. The change in the color of the block could indicate if the object is in focus or not. The camera 507 has two working modes for focusing: manual and autofocus. If the autofocus mode is chosen, the camera, through its focus sensor and optics, would automatically focus on the area of object indicated by the focus area. Because, under the preview of live images, the low resolution displaying device is often used, the status of precise focus have to be determined by the focus sensor and not by the sharpness of the live images. Then the focusing status is indicated in the frame of live pictures with symbol, for example the color of the focus block or audible sound. If the manual focus mode is selected, it is often used to image an object at a predetermined distance. When the optics in the front of camera 507 is factory calibrated to provide a predetermined (fixed) focusing distance for the camera, the users could then move the camera 507 (holding the imaging apparatus) back and forth while using the focus sensor indicator 512 as the guidance. If the focal length of the optics is also fixed, or a lens with fixed focal length is used, then the optical magnification of the imaging system is also fixed in such circumstance. With the help of focus sensor, the optics lens with the fixed focusing distance and the fixed optical focus length would enable the user to take pictures with fixed magnification, which is important if the geometrical measurement is to be taken later from the captured images.

As shown in FIG. 5, the special optics is used in the front of lighting unit 508 to generate a focused light beam, with its beam waist (narrowest part of the beam or focus of the beam) located at a predetermined distance from the camera 507. As an example shown in the FIG. 5, when a human eye 501 is located at the predetermined distance, the light beam from the lighting unit 508 is also focused near the area, but at a small distance from the optical axis of the camera 507. The picture 503 presents a separate view seen from the camera 507 when the eye is photographed. The circle 513 in the center of the picture 503 indicates the opening of the iris from an eye. Here, the light beam from the lighting unit 508 is focused and projected into the eye from the edge of the iris opening whose location is indicated by spot 514 in the picture 503. Such arrangement is very useful in providing a special lighting condition, called retroillumination, and allows users to observe cataract in the eye easily.

On other hand, the light from the lighting unit 509 forms a divergent beam and with its axis almost in parallel with the optical axis of the camera 507. The divergence of the light beam ensures that the object within the field of view of the camera 507 is well illuminated. Using the close proximity between the light source 509 and the camera 507, such lighting arrangement allows users to exam objects in narrow space or in the closed cavities. When an eye is photographed in close distance with illumination from the lighting unit 509, it creates a "shadowless" image as shown in the picture 503, where the bright spot 515 represents the spectacular reflection from the cornea. Such lighting condition created by the unit 509 could also be used as the supplementary "background" lighting for photographing cataract in the eye under the retroillumination. Again, the focus indication block 516 is shown in picture 503, which could be used to focus precisely onto the cataract seen in the crystalline lens. In another special application, when a visible or an invisible (IR) light emitter is used in the lighting unit 409, the facial images of a patient taken at distance from the camera 507 could be used to diagnoses a medical condition called amblyopia. The light from the unit 509 creates a diffused reflection of light from the retina area and then back through the irises of the patients, is often seen as "red eye" in the facial images. If the reflections of light from two eyes are not symmetric as appeared in the irises, it indicates possible eye problem for the patient. Additional potential applications for such imaging system include photographing cavities in the ear, month, and nose of patients.

Figure 6A:
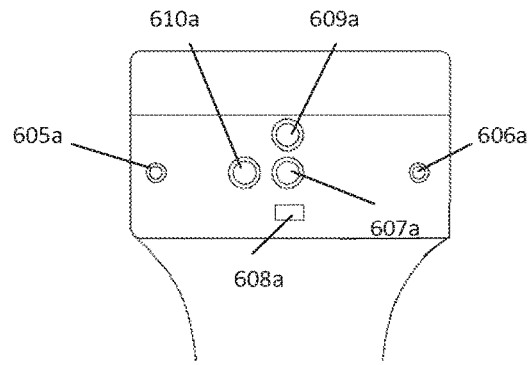
FIG. 6a is the preferred embodiment of an exterior imaging subsystem with stereoscopic (3D) imaging capability.
Figure 6B:
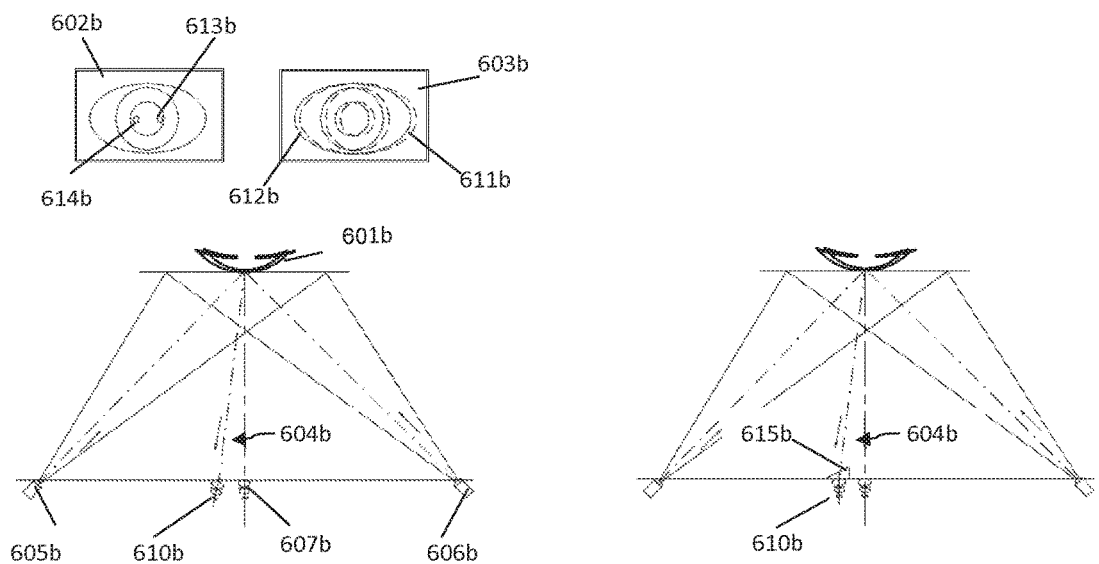
FIG. 6b shows the schematics of the special lighting system for the stereoscopic exterior imaging subsystem, and two embodiments of the optical designs for implementing the stereoscopic imaging capability as a supplementary to a 2D imaging system.

The exterior imaging subsystem shown in FIG. 5 uses only single camera 507. FIGS. 6a and 6b show an embodiment with two cameras in order to take the stereoscopic images. The stereoscopic images have the advantage of displaying depth information, and are better in visualizing the transparent medium, like the cornea. As shown in FIG. 6a, the lighting unit 605a, 606a, 608a, 609a consist of same lighting elements of lighting unit 405, 406, 408, 409 which are described in FIG. 4, and behave in same way too. Meanwhile, the camera 607a is also constructed with same optics and could perform same tasks as the camera 407 shown in FIG. 4. Next to the camera 607a, a new camera 610a added and is to be operated in synchronization with camera 607a. In other words, the shutters for both camera 607a and 610a should be opened and closed at same time. Together, camera 607a and 610a generate pictures in the similar fashion as two eyes of human being, when they are focused at same object. FIG. 6b shows the details of the lighting schematic for the same imaging system represented in FIG. 6a, where 605b, 606b, 607b and 610b are same components as 605a, 606a, 607a and 610a respectively. The photographed object 601b, an eye for example, is located near the convergent point of light beams from unit 605b and 606b, as well as at the convergent point of the optical axes of two camera 607b and 610b. The convergent angle 604b, formed by the optical axes of two cameras, could be either fixed or adjustable. In case it is fixed, the distance between the object 601b and the cameras are chosen based on the size of the object in the picture 602b and 603b. Depending on the viewing conditions of the stereoscopic display system, the divergent angle 604b typically could be between 5 to 13 degrees. The image from camera 607, which represented as 611b, and camera 610b, which is represented as 612b, are combined and shown in one display 603b. Because both camera 607b and 610b are focused at the convergent point of their optical axes, if the object, here the eye, is not located exactly at the convergent point, the image 611b and 612b will not overlap to each other, as shown in picture 603b. To get proper stereoscopic images, the users need to move the imaging apparatus back and forth to get the two images coincided, as shown in the picture 602b. In the picture, the two bright spot 613b and 614b represent the spectacular reflections of light from lighting unit 605b and 606b by cornea of patient 601b. When the convergent angle 604b is fixed, the distance at which the two images from camera 607b and 610b are fully overlapped is also predetermined and fixed. Therefore, the use of dual cameras not only could generate the stereoscopic images for review, but also a precise method to set a constant distance, from the object to the cameras. As the result, the images taken at the constant distance also have same optical magnification if the focal length of the imaging optics is fixed. Such feature is important for many medical applications because the geometrical measurement could be taken later from the captured images. Even topographic profiles of the photographed objects could be calculated from the stereoscopic image pairs. It is important to point out that although the focus of the camera 607b and 610b could be pre-fixed at the convergent point of optical axes, the camera could also be set into auto focus mode during such operation.

FIG. 6b shows two possible ways the camera 610b could be implemented. In one embodiment, the optical axis and the camera 610b itself are tilted together at the convergent angle 604b from the optical axis of camera 607b. In another implementation, the camera and imaging optics for 610b are installed in parallel with that of camera 607b. Then a small optics 615b, which could be an optical wedge, is used in the front of the camera 610*b* to bend the optical axis to the required divergent angle 604*b*. If it is needed, the angle of bending could be adjusted by the optical component 615*b*.

Because the lighting unit 608*a* and 609*a* are constructed in same fashion as the unit 508 and 509, the camera 607*a* alone could also perform all of the tasks as that of camera 507 under such lighting conditions described in the previous paragraphs, including but not limiting, to the retroillumination and the background illumination. The images will be mono or nonstereoscopic. However, when the image from the camera 610*a* is added, the stereoscopic image pairs are generated for the same imaging applications, providing depth information to the users for the first time.

It is important to point out that the exact locations of component 608*a*, 609*a* and 610*a* do not have to be same as shown in FIG. 6*a*. For example, camera 610*a* could be located at the right hand side of camera 607*a*, and still functions well. Their positions and patterns could be arranged in other fashions, as long as their relative positions and distances to the camera 607*a* are close to what are shown in FIG. 6*a*.

Figure 7A:
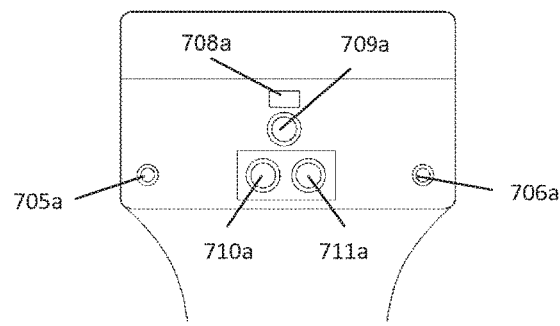
FIG. 7a is the preferred embodiment of an exterior imaging subsystem where the imaging optics/system is designed as stereoscopic (3D) only.
Figure 7B:
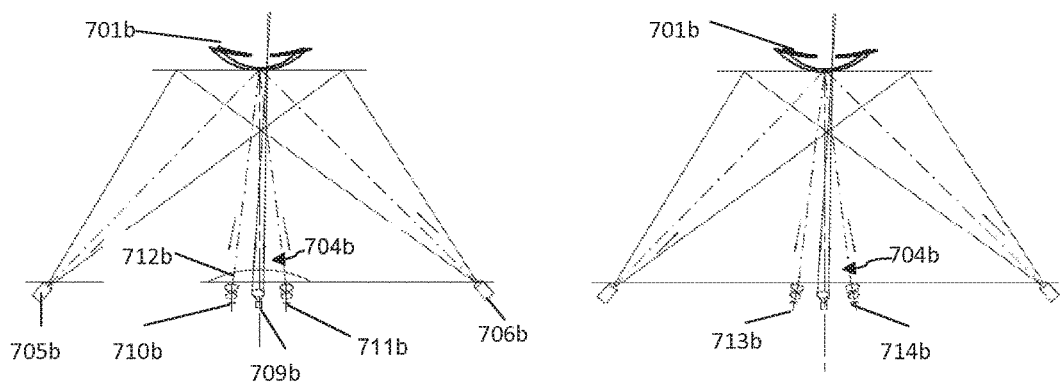
FIG. 7b shows the schematics of the special lighting system for the stereoscopic exterior imaging subsystem, and two embodiments of the optical implementations for the stereoscopic imaging system.

A different implementation of the stereoscopic exterior imaging subsystem is shown in FIG. 7*a*, which could perform same functions as the one demonstrated in FIG. 6*a*. In this new design, the lighting unit 705*a*, 706*a*, 708*a* and 709*a* consist of same lighting element of the unit 605*a*, 606*a*, 608*a* and 609*a*, and work in same fashions too. The stereoscopic camera pair 710*a* and 711*a* are synchronized and would work the same way as the camera pair 607*a* and 610*a* in order to generate the stereoscopic image pairs. However, the construction of the stereoscopic camera module is different. As shown in FIG. 7*b*, a special optics 712*b* is placed in the front of ordinary imaging optics of camera 710*b* and 711*b*, which are same cameras of 710*a* and 711*a* shown in FIG. 7*a*. The imaging optics and camera for module 710*b* and 711 *b* are installed with their optical axes in parallel, but separated with a distance. The optics 712*b* would cause the bending of optical axes from the module 710*b* and 711*b* symmetrically and form a convergent angle 704*b* toward the imaged object 701*b*. The optics 712*b* could be in the form of sphericalplano lens or double wedge prism. The optical bending power of the optical element 712*b* could be either fixed or adjustable, and resulting in either a fixed divergent angle or an adjustable divergent angle 704*b*. The second embodiment in FIG. 7*b* demonstrates a design of the stereoscopic imaging module with the fixed divergent angle 704*b*, which is formed by tilting the optical axes of the imaging optics and the camera for both module 713*b* and 714*b*.

Figure 8:
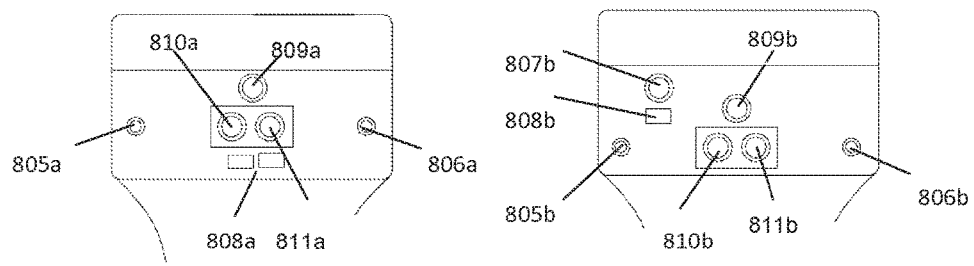
FIG. 8 demonstrates two additional embodiments of the stereoscopic exterior imaging subsystem. One embodiment comes with the combination of one stereoscopic imaging system and one 2D imaging system.

Two more embodiments for the stereoscopic exterior imaging subsystem are shown in FIG. 8, which are variants of embodiments shown in FIG. 7*a*. The imaging subsystem formed by the lighting unit 805*a*, 806*a*, 808*a* 809*a* and the stereoscopic imaging module 810*a* and 811*a* behaves same as the one with lighting unit 705*a*, 706*a*, 708*a*, 709*a* and camera 710*a* and 711*a* shown in FIG. 7*a*. The two subsystems are different only in the locations of the lighting unit 808*a* and 809*a*. Also two lighting elements are used for the lighting unit 808*a* to increase the luminance on the imaged object. In the second embodiment, one stereoscopic imaging module, which consists of the lighting unit 805*b*, 806*b*, 809*b* and the camera 810*b*, 811*b*, is combined with one mono imaging module, which consists of lighting unit 808*b* and camera 807*b*, to form the exterior imaging subsystem. The lighting unit 809*b*, similar to 809*a* and 709*b* in FIG. 7*b*, produces focused light beam for the retroillumination application. Meanwhile, under the illumination of the divergent light beam from the lighting unit 808*b*, the mono camera 807*b* could be used in imaging applications where stereoscopic images are not required. The emitted light from the lighting unit 808*b* could be visible or invisible to human eyes. The camera 807*b* could also be operated in either manual focus or auto-focus mode too. The stereoscopic imaging modules shown in FIG. 8, which consists of the camera 810*a*, 811 *a* and 810*b*, 811 *b*, could be constructed from the optical design described either for the camera 7010*b* and 711*b*, or 713*b* and 714*b* in FIG. 7*b*.

It is important to point out that the portable eye imaging apparatus discussed in this patent could be built with the posterior imaging subsystem only, or combined with any of exterior imaging subsystems discussed or even portion of the exterior imaging subsystem. An imaging apparatus with only the exterior imaging system could also be considered.

Figure 9:
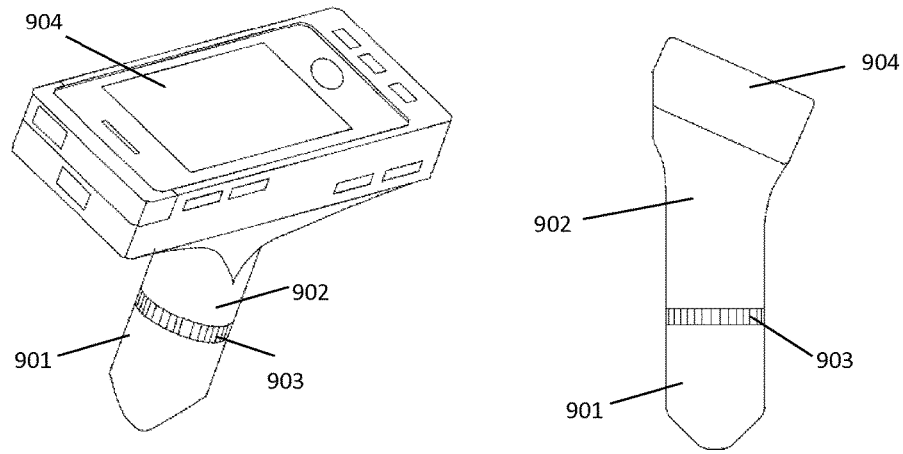
FIG. 9 is another embodiment of the portable eye imaging apparatus where the touch-screen display is mounted differently and with a lock ring for securing the posterior imaging subsystem.

Another embodiment for the portable eye imaging apparatus is shown in FIG. 9, which is constructed in almost same way as the one demonstrated in FIG. 3. It also consists of two main subsystems: the removable posterior eye imaging subsystem 901 and the portable computing/communication subsystem 902. The described portable imaging apparatus is capable of imaging both the posterior and anterior portion of the eye, with same and/or different optical system(s) and the digital image capturing system(s). The removable posterior eye imaging subsystem 901 could be detached from the subsystem 902 after it is unlocked from the locking ring 903. The use of the locking ring 903 not only prevents accidental removal of the subsystem 901 and but also seals the gaps between two subsystems in case a water-tight sealing is required. Such mechanism of locking ring could also be used in the embodiment demonstrated in FIG. 3. The portable computing device 904 (same as 304 in FIG. 3) is mounted on top of the computing/communication subsystem 902 at an inclined angle, shown in FIG. 9, for allowing easier operation of the device 904 by the users. The direction of the inclined surface is different between embodiments shown in FIG. 9 and the one shown in FIG. 3. The advantage of new embodiment is to allow users to view the video images in more natural way when the wider side of the display is oriented from left hand to right hand for the users. The short coming of such orientation is that the wide edge of the screen could block the view of the users from seeing the photographed object directly. Another embodiment of the invention is to build the imaging apparatus in one piece and with subsystem 901 attached to subsystem 902 permanently.

Figure 10:
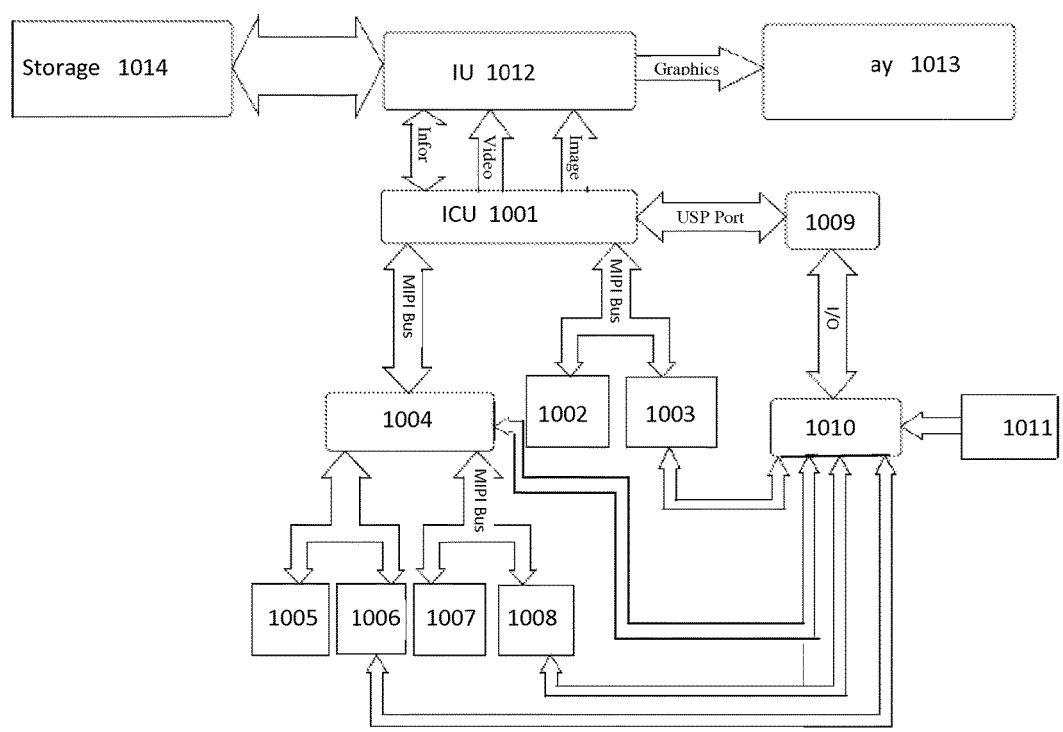
FIG. 10 is the detailed system schematic diagram for the whole imaging system based on portable computing devices. It shows the control schematics and data flow in the imaging system.

The standard portable computing device, like a smart phone, often has limited numbers of imaging and lighting elements. To extend its ability to control and drive multiple cameras and solid state lighting devices, a more sophisticated electronic system must be built around it. FIG. 10 demonstrates an embodiment where the imaging apparatus is built around the portable computing device (ICU) 1001. A digital imaging sensors 1002 and a solid state lighting unit 1003 interfacing with the computing device 1001 through the standard data bus, which includes MIPI serial or DVP parallel output interface for the digital image sensors and communication/driving port for solid state lighting devices, form the basic imaging module for the posterior imaging subsystem described in FIG. 3. Another imaging module, which contains two digital image sensors 1005, 1007, and two solid state lighting elements 1006, 1008, interfaces with the portable computing device 1001 through a digital multiplexing module 1004. As shown in FIG. 10, the multiplexing module 1004 is built around the standard data bus for digital image sensors/lighting devices, which allows interaction between the portable computing device 1001 with individual image sensor and the lighting device. The module 1004 acts like a digital switcher, and expands the number of the image sensors and lighting devices the portable computing device 1001 could access to. The exterior imaging subsystem described for the eye imaging apparatus in FIG. 4 to FIG. 9, for example, could be connected to the portable computing device with such kind of multiplexing module. Additionally, the control of the multiplexing module 1004 could be realized through the standard I/O ports already built into the standard data bus and by the portable computing device directly. It is also important to point out that the use of multiplexing module 1004 is not mandatory if the portable computing device 1001 is already built with multiplexing capability to interface with multiple devices. The standard data bus described in this act could also include the serial or parallel port with names and standards other than MIPI and DVP as long as it provides the digital interface required for transmitting digital images. The data bus would also include the interface/channels for controlling focus motor or other actuator used in the imaging module 1002 and 1003. Although only three imaging modules, which include image sensor and lighting device, are shown in FIG. 10, it is understood that additional such modules or lighting devices, or imaging sensors could be added to the configuration.

To further expand the control capability and flexibility of portable imaging apparatus, a digital interface module 1009 is connected to the portable computing device 1001 through its standard interface port, which often is built around the standard USB port, as shown in FIG. 10. When more powerful solid state lighting devices are used, an independent driver module 1010 is also used to power and drive those solid state lighting devices, like unit 1003, 1006, 1008. The driver module 1010 could be powered by the battery in the portable computing device 1001 or a separate battery 1011 with larger capacity and larger driver current. As the result, the control of the lighting devices, as well as the control of the driver module 1010 could be carried out by the portable computing device 1001 through the I/O ports of the digital interface module 1009, as indicated by the block diagrams in FIG. 10. The multiplexing module 1004 could also be controlled through either the driver module 1010, as shown in FIG. 10, or directly from the I/O ports of the interface module 1009. Because the latency in the USB type of interface could be rather large, the control of the solid state lighting devices 1003, 1006, 1008 would be a combined effort through the interaction between the driver module 1010 and the standard data bus directly from the portable computing device 1001. For example, the setting of status and the power are provided by the driver module 1010, while the real time trigger is synchronized by the existing digital I/O ports for the lighting device in the standard data bus.

As shown in the FIG. 10, the live images captured by the imaging sensors are transmitted to the portable computing device 1001, likely in the form of RAW data format, and then processed and calibrated to form the standard video stream, which could be displayed on the small screen of the computing device 1001. The same video stream could be transmitted out of the device 1001 at same time and in real time, with or without going through a process called the video compression, and to be received by the computing apparatus (IU) 1012. The real time video stream could be either displayed on the apparatus' own display screen or an external display device 1013. The real time images could be viewed on either display devices and thus allowing the users to perform pre-view functions when the video latency is minimized. Depending on the type of the shutters used by the imaging sensors, the light from the solid state lighting devices 1003, 1006, 1008 could be either continuous or pulsed, in order to be synchronized with the opening of shutters. The video stream could also be recorded by either the portable computing device 1001 or the computing apparatus 1012. It is also understood that the video stream could also be transmitted directly to the external display device 1013 without being relayed by the computing apparatus 1012. A backup version of video stream could also be sent to the storage apparatus 1014. As stated in previous paragraphs, the data transmission or exchange among the devices 1001, 1012, 1013 and 1014 could be carried out through the wired or wireless means.

When the users trigger the shutters to take still images, the imaging sensors 1002, 1004, 1007 could be reset with different sensitivity and resolutions, while the light output from the unit 1003, 1005 1008 is also reset to coup with the new status of the imaging sensors 1002, 1004, 1007 and to be synchronized with the shutters. The data of images, in the form of RAW format, is sent to the portable computing device 1001 from the imaging sensors and then pre-processed by the image processing pipeline in order to produce high quality still images. Additional image processing algorithm, which is specific to the type of objects where the images are taken, could be applied to the images in the portable computing device 1001, or in the computing apparatus 1012 after the data is transmitted to the device. The final still images are displayed on the screen of the computing apparatus 1012 or on the external display device 1013 for the users to review. The more permanent storage of the data is kept in the storage apparatus 1014 when the still images are sent over.

The data storage apparatus 1014 is built with a computer database which keeps a copy of complete information, including the location and identification of the portable imaging apparatus, the patient's personal and medical information and time stamps/exposure parameters. The initial data entry and the updating of the patient information often are carried out at the portable computing device 1001 or the computing apparatus 1012. As shown in FIG. 10, the information is then automatically updated and synchronized among the computing devices 1001, 1012 and 1014.

Figure 11:
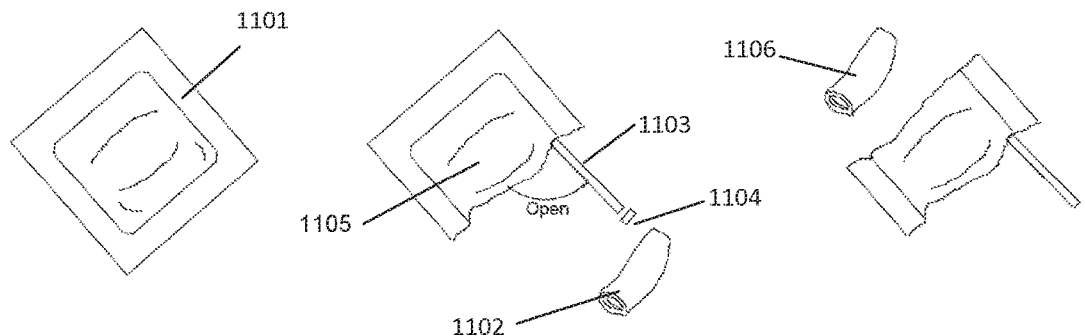
FIG. 11 is the embodiment for a disposable disinfection kit specifically made for the portable eye imaging apparatus.

Because the window of the posterior image subsystem has to contact with the patient's cornea, the window and nearby area are required to be disinfected before and after the imaging sessions, often with rubbing alcohol. Also a small amount of optically clear liquid or gel is applied to both the cornea of the patient's eye and the optical window prior to each of the imaging session. A disposable package 1101 for single use which contains sufficient index matching gel and two alcohol patches (cloth) is shown in FIG. 11. Intended to be used for one imaging session only, the content of package and the package itself are sterilized during the manufacturing process and kept sterilized. Before its use, the one side of the package is cut open, and to allow one of two alcohol patch 1102 to be ejected from the package by a small hollow tube 1103. The alcohol patch could be used to disinfect the optical window and body of the portable imaging apparatus before the imaging session. The tube 1103 could be made of plastic or other materials, and is stored inside the package during the manufacturing process by bending portion of it behind the alcohol patch 1102. When part of the package is cut open, the tube is released like a spring and sticks out of the package. As shown in the FIG. 11, one end of the tube is fit with an end cap 1104 while the other end is sealed (glued) into a flexible but sealed container (bottle) 1105 which stores the index matching gel inside. Care should be taken to insure that the container and the tube are filled with the index matching gel (liquid) fully, and there is no air bubble in the gel. After the end cap 1104 is cut off, the gel could be squeezed of from the end of the tube by compressing on the top of the container 1105. After the imaging session is finished, another side of the disposable package could be cut off to expose the second alcohol patch 1106. Both alcohol patches and the package itself could be disposed after their usages.

Figure 12:
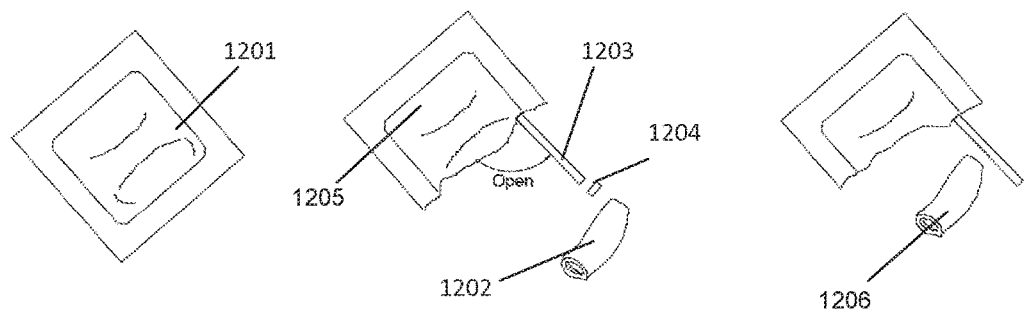
FIG. 12 is another embodiment for a disposable disinfection kit specifically made for the portable eye imaging apparatus.

Another embodiment of the similar disposable package is shown in FIG. 12, where the container for the index matching gel 1205 is placed at one end of the package 1201, instead of the middle in the previous example. Portion of the flexible tube 1203 is bent and placed between the two alcohol patches when they are sealed in the package 1201 during the manufacturing process. When one side of the package is cut off, the release of the bent flexible tube 1203 pushes out the first alcohol patch 1202. When the end cap 1204 is cut off, the index matching gel could be release by squeezing the container 1205. The second alcohol patch 1206 could be pushed out from the package 1201 then, or exposed with additional package bag is cut off, as shown in the FIG. 12.

Figure 13:
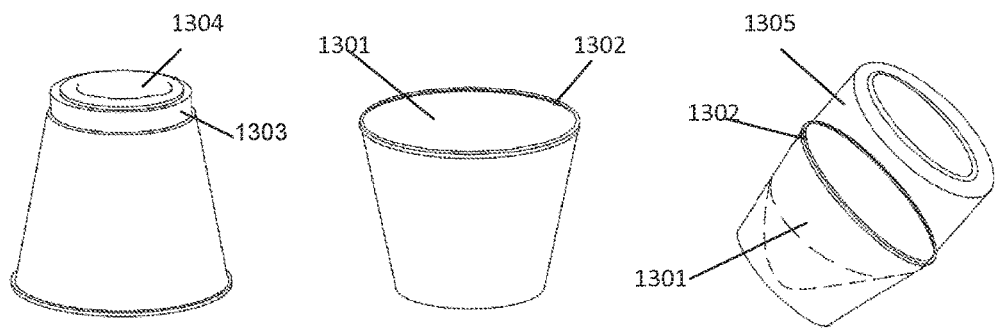
FIG. 13 is the preferred embodiment for a disposable kit specifically made for more thorough disinfection treatment of the portable eye imaging apparatus.

The optical window and surrounding area not only have to be disinfected by the alcohol before and after each imaging session, but also soaked into bleach like of chemicals solution regularly for more thorough treatment. A disposable kit of single use for such disinfection treatment is shown in FIG. 13, which could be used conveniently and directly onto the apparatus. The kit includes a cup 1301, disinfectant 1303 and alcohol patch 1304, which are sterilized and wrapped into a compact package and ready to be used at the site. The cup 1301 is made of plastic or other light weighted and flexible materials with its size fit with the external profile of the imaging apparatus. The rim of the cup 1302 is made of rubber like material and acts like a rubber band when the cup is fit onto the imaging apparatus. The disinfectant 1303 is stored in a sealed package and to be released to the cup after the seal of the package is cut off. When the cup 1301 is placed under the optical window of the imaging apparatus 1305, the window would be submerged under the disinfectant liquid. The tightened rim of the cup 1302 forms a seal around the external shell of the apparatus 1305, and prevents the liquid from spilling off by accident. After the disinfection process is finished, the alcohol patch 1304 could be taken out of its sealed package and used to clean up the chemical residue on the surface of apparatus 1305. In the embodiment shown in FIG. 13, the packages of the sealed disinfectant 1303 and the alcohol patch 1304 are placed under the bottom of the cup 1301 in the manufacturing process. It would help to save packaging space when multiple of such disposable kits are stacked up in a larger shipping box. However, the packages for the disinfectant and alcohol patch could also be placed inside the cup and even against the bottom of the cup.

The embodiments of the invention in which an exclusive property or privilege is claimed are defined as follows:

1. A hand-held eye imaging apparatus, comprising:
    an exterior imaging module configured to image an anterior segment of an eye and disposed within a first housing on an exterior surface of a second housing, wherein the second housing houses a posterior imaging module configured to image a posterior segment of the eye, the exterior imaging module comprising
    a first lighting unit comprising a first light source configured to generate a first divergent light beam to illuminate the eye;
    a second lighting unit comprising a second light source configured to generate a second divergent light beam to illuminate the eye, wherein the first lighting unit and the second lighting unit are configured to project a first center of the first divergent light beam so as to overlap a second center of the second divergent light beam at an optical axis of a camera;
    a third lighting unit positioned next to the camera, the third lighting unit comprising a third light source and a special optics in a front portion, the third lighting unit configured to generate a focused light beam to illuminate the eye, the focused light beam having a focus of the beam disposed at an edge of a pupil of the eye when the beam is projected into the eye from the edge of the pupil to create a retroillumination to observe a cataract in a crystalline lens of the eye;
    a fourth lighting unit comprising a fourth light source configured to generate a divergent light beam to illuminate the eye, the fourth lighting unit positioned close to the camera such that a fourth optical axis of the fourth lighting unit is substantially parallel with the optical axis of the camera to provide supplementary background illumination for photographing the cataract under the retroillumination; and
    the camera comprising:
        an image sensor disposed in the first housing configured to receive an image of the crystalline lens of the eye, and
        imaging optics disposed between the eye and the image sensor and configured to focus precisely onto the cataract in the crystalline lens.

2. A hand-held eye imaging apparatus comprising:
    an exterior imaging module configured to image an anterior segment of an eye and disposed within a first housing on an exterior surface of a second housing, wherein the second housing houses a posterior imaging module configured to image a posterior segment of the eye, the exterior imaging module comprising
    a first lighting unit positioned next to a camera, the first lighting unit comprising a first light source and a special optics in a front portion, the first lighting unit configured to generate a focused light beam having a focus disposed at an edge of a pupil of the eye when the beam is projected into the eye from the edge of the pupil to create a retroillumination of a crystalline lens of the eye to observe cataract in the crystalline lens;
    a second lighting unit comprising a second light source, positioned near the camera such that the second lighting unit is substantially parallel with an optical axis of the camera and configured to generate a divergent light beam to provide supplementary background illumination for photographing the cataract under the retroillumination; and
    the camera comprising:
        an image sensor disposed in the first housing configured to receive an image of the crystalline lens of the eye, and
        imaging optics disposed between the eye and the image sensor and configured to focus precisely onto the cataract in the crystalline lens.

3. The hand-held eye imaging apparatus in claim 1, wherein the focused light beam has a beam waist positioned at an edge of a pupil of the eye with a distance from the optical axis of the camera.

4. The hand-held eye imaging apparatus in claim 1, further comprising a front imaging module configured to image a posterior segment of the eye, wherein the front image module comprises a posterior light source, an optical window with a concave front surface for receiving the eye, an imaging lens disposed behind the optical window and optically aligned with the optical window, wherein the hand-held imaging apparatus further comprises a second image sensor disposed to receive a second image of the eye.

5. The hand-held eye imaging apparatus in claim 2, further comprising a front imaging module, configured to image a posterior segment of the eye, wherein the front image module comprises a posterior light source, an optical window with a concave front surface for receiving the eye, an imaging lens disposed behind the optical window and optically aligned with the optical window, wherein the hand-held imaging apparatus further comprises a second image sensor to receive a second image of the eye.

6. The hand-held eye imaging apparatus in claim 2, further comprising a front imaging module configured to image a posterior segment of the eye, wherein the front image module comprises a posterior light source, an optical window with a concave front surface for receiving the eye, an imaging lens disposed rearward the optical window and optically aligned with the optical window, wherein the hand-held imaging apparatus further comprises a second image sensor in the housing disposed to receive a second image of the eye.

* * * * *